US011142552B2

(12) United States Patent
Swain et al.

(10) Patent No.: US 11,142,552 B2
(45) Date of Patent: Oct. 12, 2021

(54) PROTEIN AGAINST FUNGAL PATHOGENS

(71) Applicant: National Institute of Plant Genome Research, New Delhi (IN)

(72) Inventors: Durga Madhab Swain, New Delhi (IN); Sunil Kumar Yadav, New Delhi (IN); Gopaljee Jha, New Delhi (IN)

(73) Assignee: National Institute of Plant Genome Research

( * ) Notice: Subject to any disclaimer, the term of this patent is extended or adjusted under 35 U.S.C. 154(b) by 0 days.

(21) Appl. No.: 16/318,504

(22) PCT Filed: Jul. 19, 2017

(86) PCT No.: PCT/IB2017/054354
§ 371 (c)(1),
(2) Date: Jan. 17, 2019

(87) PCT Pub. No.: WO2018/015895
PCT Pub. Date: Jan. 25, 2018

(65) Prior Publication Data
US 2019/0315811 A1 Oct. 17, 2019

(30) Foreign Application Priority Data
Jul. 19, 2016 (IN) .............................. 201611024726

(51) Int. Cl.
| | | |
|---|---|---|
| *C07K 1/00* | (2006.01) | |
| *C07K 14/00* | (2006.01) | |
| *C07K 16/00* | (2006.01) | |
| *C07K 17/00* | (2006.01) | |
| *C12P 21/08* | (2006.01) | |
| *A61K 39/02* | (2006.01) | |
| *C07K 14/21* | (2006.01) | |
| *A01N 25/04* | (2006.01) | |
| *A01N 25/10* | (2006.01) | |
| *A61K 9/06* | (2006.01) | |
| *A61K 9/51* | (2006.01) | |
| *A01N 63/50* | (2020.01) | |
| *A61K 38/00* | (2006.01) | |
| *A61K 39/00* | (2006.01) | |

(52) U.S. Cl.
CPC .............. *C07K 14/21* (2013.01); *A01N 25/04* (2013.01); *A01N 25/10* (2013.01); *A01N 63/50* (2020.01); *A61K 9/06* (2013.01); *A61K 9/5161* (2013.01); *A61K 38/00* (2013.01); *A61K 39/00* (2013.01)

(58) Field of Classification Search
CPC ..................................................... C07K 14/21
See application file for complete search history.

(56) References Cited

U.S. PATENT DOCUMENTS

| | | | | |
|---|---|---|---|---|
| 2012/0245080 A1* | 9/2012 | Goolsbee | ............... | A61K 9/006 514/2.5 |
| 2013/0090335 A1* | 4/2013 | Cai | ...................... | C07D 241/10 514/234.2 |
| 2016/0250167 A1* | 9/2016 | Strobel | .................. | A61K 47/44 424/93.5 |
| 2016/0250256 A1* | 9/2016 | Klingemann | .......... | A01N 63/10 424/85.2 |
| 2017/0204070 A1* | 7/2017 | Jefson | .................. | C07D 239/95 |
| 2019/0211047 A1* | 7/2019 | Van Arnam | ............. | A61P 31/10 |

FOREIGN PATENT DOCUMENTS

WO       9958833       11/1999

OTHER PUBLICATIONS

Jha et al. Genome Announc., 2015; 3(4). (Year: 2015).*
Jha et al., Genome Announcements, Jul. 23, 2015; 3(4) (Year: 2015).*
CDC, https://www.cdc.gov/fungal/diseases/index.html, accessed May 25, 2020 (Year: 2020).*
Almeida et al., Frontiers in Microbiology (Mini Review), 2019; 10(214): 1-5 (Year: 2019).*
Burgess et al., J. of Cell Bio. 111:2129-2138, 1990 (Year: 1990).*
Lazar et al., Molecular and Cellular Biology, 1988, 8:1247-1252 (Year: 1988).*
Kleppe et al., Tidsskr Nor Laegeforen, Sep. 30, 2001; 121(23):2717-20; Abstract only (Year: 2001).*
Hoppner, Horm Re. 2002, 58 Suppl. 3:7-15; Abstract only (Year: 2002).*
Lodish et al., Mol. Cell Biol., 3rd ed. Scientific American Books, NY, 1995 (Year: 1995).*
Bowie et al. (Science, 1990, 257:1306-1310) (Year: 1990).*
Seo et al., Journal of Bacteriology, 2011; 193(12):3149 (Year: 2011).*
Lim et al., Journal of Bacteriology, 2009; 191(11): 3758-3759 (Year: 2009).*
Andersen JB, Koch B, Nielsen TH, Sørensen D, Hansen M, Nybroe O, Christophersen C, Sørensen J, Molin S, Givskov M (2003) Surface motility in *Pseudomonas* sp. DSS73 is required for efficient biological containment of the root-pathogenic microfungi *Rhizoctonia solani* and *Pythium ultimum*. Microbiology 149: 37-46. 2003.

(Continued)

*Primary Examiner* — Gary B Nickol
*Assistant Examiner* — Lakia J Jackson-Tongue
(74) *Attorney, Agent, or Firm* — Belles Katz LLC

(57) ABSTRACT

The present invention relates to a novel protein comprising novel genes that is extracted from *Burkholderia gladioli* strain NGJ1. A nucleotide sequence encoding the novel protein is represented by sequence SEQ ID No. 1 and amino acid sequence of the novel protein is represented by the sequence SEQ ID No. 2 is further provided. A nucleotide sequence and the amino acid sequence are obtained from genetically engineered Bg_9562 gene. The novel protein as well as encoding gene is adapted for broad spectrum antifungal and mycophagous activities.

12 Claims, 4 Drawing Sheets

Specification includes a Sequence Listing.

(56) References Cited

OTHER PUBLICATIONS

Beneduzi A, Ambrosini A, Passaglia LMP (2012) Plant growth-promoting rhizobacteria (PGPR): Their potential as antagonists and biocontrol agents. Genetics and Molecular Biology 35: 1044-1051.
Compant S, Duffy B, Nowak J, Clément C, Barka EA (2005) Use of plant growth-promoting bacteris for biocontrol of plant disease: Principles, mechanism of action, and future prospects. Appl Environ Microbiol. 71:4951-4959.
Elshafie HS, Camele I, Racioppi R, Scrano L, Iacobellis NS, Bufo SA (2012) In vitro antifungal activity of Burkholderia gladioli pv. agaricicola against some Phytopathogenic fungi. Int J Mol Sci. 13: 16291-16302.
Ghosh S, Gupta SK, Jha G (2014) Identification and functional analysis of AG1-IA specific genes of Rhizoctonia solani. Curr Genet. 60: 327-341. 2014.
Hane JK, Anderson JP, Williams AH, Sperschneider J, Singh KB (2014) Genome Sequencing and Comparative Genomics of the Broad Host-Range Pathogen *Rhizoctonia solani* AG8. PLoS Genet, doi: 10.1371/journal.ogen.1004281.
Huang X, Zhang N, Yong X, Yang X, Shen Q (2012) Biocontrol of Rhizoctonia solani damping-off disease in cucumber with Bacillus pumilus SQR-N43. Microbiol Res 167: 135-143.
Jha G, Tyagi I, Kumar R, Ghosh S (2015) Draft Genome Sequence of Broad-Spectrum Antifungal Bacterium *Burkholderia gladioli* Strain NGJ1, Isolated from Healthy Rice Seeds. Genome Announc. doi: 10.1128/genomeA.00803-15.
Raaijmakers JM, Mazzola M (2012) Diversity and Natural Functions of Antibiotics Produced by Beneficial and Plant Pathogenic Bacteria. Annu Rev Phytopathol. 50: 403-424.
Reinhold-Hurek B, Hurek T (2011) Living inside plants: bacterial endophytes. Curr Opin Plant Biol. 14:435-443.
Schäfer A, Kalinowski J, Simon R, Seep-Feldhaus AH, Pühler A (1990) High-frequency conjugal plasmid transfer from gram-negative *Escherichia coli* to various gram-positive coryneform bacteria. J Bacteriol. 172(3):1663-1666.
Schäfer A, Tauch A, Jäger W, Kalinowski J, Thierbach G, Pühler A (1994) Small mobilizable multi-purpose cloning vectors derived from the *Escherichia coli* plasmids pK18 and pK19: selection of defined deletions in the chromosome of Corynebacterium glutamicum. Gene 145(1):69-73.
Tan Z, Lin B, Zhang R (2013) A novel antifungal protein of Bacillus subtilis B25. Springer Plus 2:543. doi: 10.1186/2193-1801-2-543.
Tortora ML, Diaz-Ricci JC, Pedraza RO (2011) Azospirillum brasilense siderophores with antifungal activity against Colletotrichum acutatum. Archives of Microbiology 193: 275-286.
Wong JH1, Hao J, Cao Z, Qiao M, Xu H, Bai Y, Ng TB (2008) An antifungal protein from Bacillus amyloliquefaciens. J Appl Microbiol. 105(6):1888-1898.
Yadav V, Mandhan R, Kumar M, Gupta J, Sharma GL (2010) Characterization of the *Escherichia coli* Antifungal Protein PPEBL21. Int J Microbiol. 196363. doi: 10.1155/2010/196363.
Zheng A, Lin R, Zhang D, Qin P, Xu L, Ai P, Ding L, Wang Y, Chen Y, Liu Y, et al. (2013) The evolution and pathogenic mechanisms of the rice sheath blight pathogen. Nat Commun. 4:1424. doi: 10.1038/ncomms2427.
Tang-Bing Cui, Hai-Yun Chai, Li-Xiang Jiang. (2012) Isolation and Partial Characterization of an Antifungal Protein Produced by Bacillus licheniformis BS-3 Molecules. 17(6):7336-7347.
Haas D, Défago G (2005) Biological control of soil-borne pathogens by fluorescent pseudomonads. Nat Rev Microbiol. 3: 307-319.
Frey-Klett P, Burlinson P, Deveau A, Barret M, Tarkka M, Sarniguet A (2011) Bacterial-Fungal Interactions: Hyphens between Agricultural, Clinical, Environmental, and Food Microbiologists. MMBR. 75(4):583-609. doi:10.1128/MMBR.00020-11.
Kishore GK, Pande S, Podile AR (2005) Biological control of collar rot disease with broad-spectrum antifungal bacteria associated with groundnut. Can J Microbiol. 51:123-132.
Leveau JHJ, Preston GM (2008) Bacterial mycophagy: definition and diagnosis of a unique bacterial-fungal interaction. New Phytol. 177: 859-876.
Li J, Yang Q, Zhao L, Zhang S, Wang Y, Zhao X (2009) Purification and characterization of a novel antifungal protein from Bacillus subtilis strain B29. Journal of Zhejiang University Science B. 10(4):264-272.doi:10.1631/jzus. B0820341.
Lugtenberg B, Kamilova F (2009) Plant-growth-promoting rhizobacteria. Annu. Rev. Microbiol.63:541-556.
Manwar AV, Khandelwal SR, Chaudhari BL, Meyer JM, Chincholkar SB (2004) Siderophore production by a marine Pseudomonas aeruginosa and its antagonistic action against phytopathogenic fungi. Appl Biochem Biotechnol. 118: 243-251.
Mela F, Fritsche K, de Boer W, van Veen J a, de Graaff LH, van den Berg M, Leveau JHJ (2011) Dual transcriptional profiling of a bacterial/fungal confrontation: Collimonas fungivorans versus Aspergillus niger. ISME J. 5: 1494-1504.
Nagarajkumar M, Bhaskaran R, Velazhahan R (2004) Involvement of secondary metabolites and extracellular lytic enzymes produced by Pseudomonas fluorescens in inhibition of *Rhizoctonia solani*, the rice sheath blight pathogen. Microbiol Res. 159:73-81.
Höppener-Ogawa S, Leveau JHJ, van Veen J a, De Boer W (2009) Mycophagous growth of Collimonas bacteria in natural soils, impact on fungal biomass turnover and interactions with mycophagous Trichoderma fungi. ISME J. 3: 190-198.
Wong et al., An antifungal protein from Bacillus amyloliquefaciens. Journal of Applied Microbiology ISSN 1364-5072. (2008) CN.
L S Chernin et al., Molecular cloning, structural analysis, and expression in *Escherichia coli* of a chitinase gene from Enterobacter agglomerans, Applied and Environmental Microbiology, Mar. 1, 1997 (Mar. 1, 1997), pp. 834-839. US.
International Search Report from corresponding Application No. PCT/IB2017/054354, dated Dec. 8, 2017. WO.
Durga Madhab Swain et al., A prophage tail-like protein is deployed by Burkholderia bacteria to feed on fungi, Nature Communications I8:404, Article, DOI: 10.1038/s41467-017-00529-0.
Haung D, Ou B, Prior RL (2005) The chemistry behind antioxidant capacity assays. J. Agric.Chem. 53:1841-1856.
Meshulam T, Levitz SM, Christin L, Diamond RD (1995) A simplified new assay for assessment of fungal cell damage with the tetrazolium dye, (2,3)-bis-(2-methoxy-4-nitro-5-sulphenyl)-(2H)-tetrazolium-5-carboxanil ide (XTT). J Infect Dis. 4:1153-1160.
Afsharmanesh H. et al., "Biocontrol of Rhizoctonia solani, the causal agent of ben damping-off by fluorescent pseudomonads", NCBI—www.ncbi.nlm.nih.gov/pubmed/17390854, Commun Agric Bio Sci., Nov. 4, 2019, (2006); 71 (3PtB):pp. 2, Abstract only.
Sharifi-Tehrani A. et al., "Biological Control of Tiarosporella Phaseolina the Causal Agent of Charcoal Rot of Soybean",PubMed—NCB—wwww.ncbi.nlm.nih.gov/pubmed/16637176, Commun Agric Appl Biol Sci, Nov. 4, 2019, (2005); 70(3) pp. 1, Abstract Only.

* cited by examiner

```
                        SEQUENCE LISTING

<160> NUMBER OF SEQ ID NOS: 2

<210> SEQ ID NO 1
<211> LENGTH: 333
<212> TYPE: DNA
<213> ORGANISM: Burkholderia gladioli strain NGJ1
<220> FEATURE:
<221> NAME/KEY: CDS
<222> LOCATION: (1)..(333)

<400> SEQUENCE: 1
atgaacacgg aaaaccagga tccgacgagc accagcgaca acgccgcgaa cacgcacacg      60
ctcgacacgc cgctcgcgcg cggcgagcag acgatcaccc aggtgacgct ggccaagccc     120
gatgccggcg cgctgcgcgg cacctcgctg tcggcgctcg tcaacctcga cgtcgacgcg     180
ctgtgcaagg caactccgcg cgctacgagc ccggcggtca ccgcggccga catccgcgcc     240
atggaccccg ccgacgcaat ctcggtcgga ggcatcttcg ccggttttgt tatgccgaag     300
tcgatcaaag cgagcatgga atccccgagc gcg                                  333

<210> SEQ ID NO 2
<211> LENGTH: 111
<212> TYPE: PRT
<213> ORGANISM: Burkholderia gladioli strain NGJ1
<220> FEATURE:
<221> NAME/KEY: PRT
<222> LOCATION: (1)..(111)
```

-continued

```
<400> SEQUENCE: 2

Met Asn Thr Glu Asn Gln Asp Pro Thr Ser Thr Ser Asp Asn Ala Ala
1               5                   10                  15

Asn Thr His Thr Leu Asp Thr Pro Leu Ala Arg Gly Glu Gln Thr Ile
            20                  25                  30

Thr Gln Val Thr Leu Ala Lys Pro Asp Ala Gly Ala Leu Arg Gly Thr
        35                  40                  45

Ser Leu Ser Ala Leu Val Asn Leu Asp Val Asp Ala Leu Cys Lys Ala
    50                  55                  60

Ile Pro Arg Ala Thr Ser Pro Ala Val Thr Ala Ala Asp Ile Arg Ala
65                  70                  75                  80

Met Asp Pro Ala Asp Ala Ile Ser Val Gly Gly Ile Phe Ala Gly Phe
                85                  90                  95

Val Met Pro Lys Ser Ile Lys Ala Ser Met Glu Ser Pro Ser Ala
            100                 105                 110
```

PROTEIN AGAINST FUNGAL PATHOGENS

CROSS-REFERENCE TO RELATED PATENT APPLICATIONS

The present application is a U.S. national stage application under 35 U.S.C. § 371 of PCT Application No. PCT/IB2017/054354, filed Jul. 19, 2017, which claims priority to Indian Application No. 201611024726, filed Jul. 19, 2016, the entireties of which are incorporated herein by reference.

FIELD OF INVENTION

This invention relates to a novel protein against fungal pathogens. More specifically, the present invention relates to the novel protein from *Burkholderia gladioli* strain NGJ1 against fungal pathogens for controlling wide variety of fungal diseases.

BACKGROUND OF THE INVENTION

Bacteria are omnipresent that are found in soil, water, air etc. and also within multicellular organisms that include insects, plants and animals. They have very active cell to cell communication system and sometimes can behave as multicellular organisms by forming biofilms. For survival, they need to compete with other co-habiting bacteria, fungi etc. and have to live within or in association with plants, animals etc (Frey-Klett et al, 2011; Reinhold-Hurek and Hurek, 2011). The interaction of bacteria with other organisms can be mutualistic, commensalistic, antagonistic or parasitic (Haas and Défago, 2005; Frey-Klett et al, 2011). Conventionally, they directly promote plant growth by synthesizing phytohormones etc. or indirectly help plants by protecting them from potential pathogenic microorganisms (Haas and Défago, 2005; Lugtenberg and Kamilova, 2009; Beneduzi et al, 2012).

Bacteria demonstrating antagonistic interactions are being considered as potential biocontrol agents. The mechanism of biocontrol is generally attributed to production of antifungal metabolites (bacillaene, difficidin, fengycin, macrolactin, surfactin etc.), chitinolytic enzymes, siderophores, toxins etc. by the bacteria (Huang et al, 2005; Tortora et al, 2011; Raaijmakers and Mazzola, 2012). Interestingly, among antifungal bacteria, there are few species that can grow and multiply at the cost of growing fungal biomass. Such interaction is called bacterial mycophagy (Leveau and Preston, 2008). One of the first direct evidence of bacterial mycophagy has been reported for Collimonas which without any added nutrients could grow in the autoclaved soil, in the presence of actively growing mycelium of three common dune soil invading fungi i.e. *Chaetomium globosum, Fusarium culmorum*, and *Mucorhiemalis* (Höppener-Ogawa et al, 2009).

*Burkholderia* spp. is rod-shaped Gram-negative bacteria that are found in diverse habitats. Few among them have been reported to be pathogenic to plants and humans; however, a few having potential activities towards plant growth-promoting, endophytic, and antifungal strains have also been reported. Recently, gene sequencing of bacterium *Burkholderia gladioli* strain NGJ1 from the rice seedlings has been carried out (Jha et al, 2015). *Rhizoctonia solani* is one of the important soil borne fungal pathogen which is causal agent of several economically important diseases in various crop plants, including rice (Zheng et al, 2013; Ghosh et al, 2014; Hane et al, 2014). It is considered to be a grave yard of rice cultivation. However, it is noteworthy that several bacterial species including *Burkholderia, Actinomycetes, Bacillus, Psuedomonas* etc. are known to be antifungal against *R. solani* (Andersen et al, 2003; Elshafie et al, 2012; Huang et al, 2012; Mela et al, 2012).

These biocontrol agents are potentially useful in providing environmental and eco-friendly alternatives of chemical fungicides for controlling various plant diseases; however there are yet limitations to utilize them directly. Some of biocontrol bacteria produce lytic compounds as extracellular lytic enzymes, siderophores, salicylic acid, antibiotics, and volatile metabolites, such as hydrogen cyanide (Nagarajkumar et al, 2004; Manwar et al, 2005; Compant et al, 2005; Kishore et al, 2005; Sharifi et al, 2005; Afsharmanesh et al, 2006) as antifungal agents. Apart from this, many novel antifungal proteins such as Baciamin, produced by *Bacillus amyloliquefaciens* (Wong et al, 2008), B29I, produced by *B. subtilis* strain B29 (Li et al, 2009), F2 protein, produced by *B. licheniformis* (Tang-Bing et al, 2012), PPEBL21 protein, produced by *Escherichia coli BL*21 (Yadav et al, 2012) and a hypothetical protein (gi154685475) produced by *B. subtilis* B25 (Tan et al, 2013) demonstrated inhibitory effect against various plant pathogens.

Korean published application KR 200641054 relates to a method for inhibiting anthracnose disease by using a culture solution of a strain of Bacoliella gladiolis NIAB 131-133 having antimicrobial activity and a method for inhibiting anthracnose causing fungi (*Colletotrichum gloeosporioides*) using culture solution of the bacterial strain *Bacillaria gladioli* NIAB 131-133. The bacterium strain works against the fungal strains but are not specific for rice plants and related diseases.

Japanese published application JP2010047532 provides a novel means using microorganisms of the genus *Burkholderia* as plant disease control method characterized by spraying a microorganism belonging to the genus *Burkholderia* and exhibiting an antibacterial action against plant pathogens on the foliage of a plant, and a plant disease control method for controlling the microorganisms of genus *Burkholderia.*

However, in spite of extensive global effort, till date no source of complete disease resistance has been identified for sheath blight disease of rice caused by *Rhizoctonia solani*. Further, no proper control measures are developed for *Rhizoctonia solani*, which can also be useful for controlling several other diseases caused by *R. solani* on various important crop plants. Moreover, besides *R. solani*, plants are susceptible to several other fungal pathogens. To control them in an environmental friendly manner still remains a challenge. Hence developing strategy for broad spectrum antifungal compounds would be helpful to control fungal diseases of diverse plants/crops.

To overcome the above mentioned problems, the present invention provides a genetically engineered gene sequence of *Burkholderia gladioli* strain NGJ1. The bacterial overexpressed and purified protein showed antifungal activity against *R. solani*. Furthermore, the purified protein exhibits broad-spectrum antifungal activity against several agriculturally important pathogens including *Magnaporthe oryzae, Venturia inaequalis, Alternaria brassiceae, Fusarium oxysporum*, Dedymella sp., *Phytophthora* sp, *Colletotrichum* sp., *Ascochyta rabiei*, Neofusicoccum sp., *Alternaria* sp., *Saccharomyces cerevisiae* and *Candida albicans.*

SUMMARY OF INVENTION

In one embodiment of the invention, a novel protein comprising novel genes that is extracted from *Burkholderia* gladioli strain NGJ1 is provided. A nucleotide sequence encoding the novel protein is represented by sequence SEQ ID No. 1 and amino acid sequence of the novel protein is represented by the sequence SEQ ID No. 2.

In another embodiment, the nucleotide sequence and the amino acid sequence are obtained from genetically engineered Bg_9562 gene. In an embodiment, the nucleotide sequence encoding the novel protein is at least 70% identical to the nucleotide sequence of SEQ ID No. 1 or the amino acid sequence represented by SEQ ID No. 2. In another embodiment, the nucleotide sequence of SEQ ID NO: 1 have at least 1 to 90 nucleotide acid substitutions, deletions, and/or insertions. In another embodiment, the amino acid sequence of SEQ ID NO: 2 have at least 1 to 30 amino acid substitutions, deletions, and/or insertions. In another embodiment, the amino acid sequence of SEQ ID NO: 2 varies by 11 amino acid substitutions.

In one embodiment, the novel protein is adapted for broad spectrum anti-fungal activities and produces high mass production of proteins. In another embodiment, the amino acid sequence of the novel protein is of 111 amino acid residues long with molecular weight of ~13 kDa, a pI of about 4.65 and a pH optimum at about 7.4.

In another embodiment, the protein is adapted with anti-fungal and mycophagous activity that inhibits growth of fungal sclerotia and induces cell death in fungal mycelia. In another embodiment, the antifungal activity of Bg_9562 gene is useful for controlling sheath blight diseases of rice and other crops caused by *Rhizoctonia solani*.

In another embodiment, a method to prepare novel protein by SEQ ID No. 2 with antifungal activity is provided. The method comprises the steps of: (i) identification of the novel protein possessing anti-fungal and mycophagous activity from *Burkholderia gladioli* strain NGJ1, (ii) gene sequence and protein sequence is evolved by artificially synthesizing the identified protein of step (i) and incorporating the desired gene change in the identified protein to synthesize gene through gene synthesis, (iii) the evolved protein is over expressed in pET28a expression vector, (iii) the overexpressed protein is purified by Ni-NTA affinity chromatography, (iv) the purified protein is assessed for antifungal activity and (v) antifungal nature of the protein is established by reverse genetics approach. The recombinant expression of the novel protein prevents the growth of fungal sclerotia, induces cell death in fungal mycelia and treats some human/animal diseases.

In another embodiment, a composition from novel peptide is provided. The components of the composition comprises of oil that are selected from the group comprising of almond oil, rapeseed oil and sesame oil; thickeners that are selected from beeswax, cocoa butter and shea butter, emulsifiers selected from the group comprising of alcohols such as cetyl alcohol; and water.

In another embodiment, the composition encoding novel peptide is adapted to develop broad spectrum fungal disease resistance wherein the fungus is selected from the group comprising of *Rhizoctonia solani, Alternaria brassicae, Magnaporthe oryzae, Venturia inaequalis, Fusarium oxysporum, Dedymella* sp., *Phytophthora* sp, *Colletotrichum* sp., *Ascochyta rabiei, Neofusicoccum* sp., *Alternaria* sp., *Saccharomyces cerevisiae* and *Candida albicans*

In another embodiment, a process to prepare the composition is provided. The process comprises the steps of: (i) Bg_9562 protein is produced in bulk quantities by fermentation using bioreactor, (ii) the fermented product obtained is encapsulated by chitosan or non-chitosan based nanoparticles; and (iii) the encapsulated products of step (ii) is used to develop a water base or an oil base cream/ointment and, (iv) the product of step (iii) are further developed to prepare antifungal films comprising starch/oils.

In another embodiment, the method to control fungal disease of plants or crops is provided by applying a polypeptide comprising the sequence of SEQ ID NO: 1 or 2, or a composition, to an infected plant, infected plant part, or infected crop, humans and animals that are at risk of fungal infection.

In another embodiment, the protein is produced by expressing its encoding nucleotide in the cells of bacteria, yeast, insects, plants, humans or animals using recombinant DNA technology.

Figure 6:
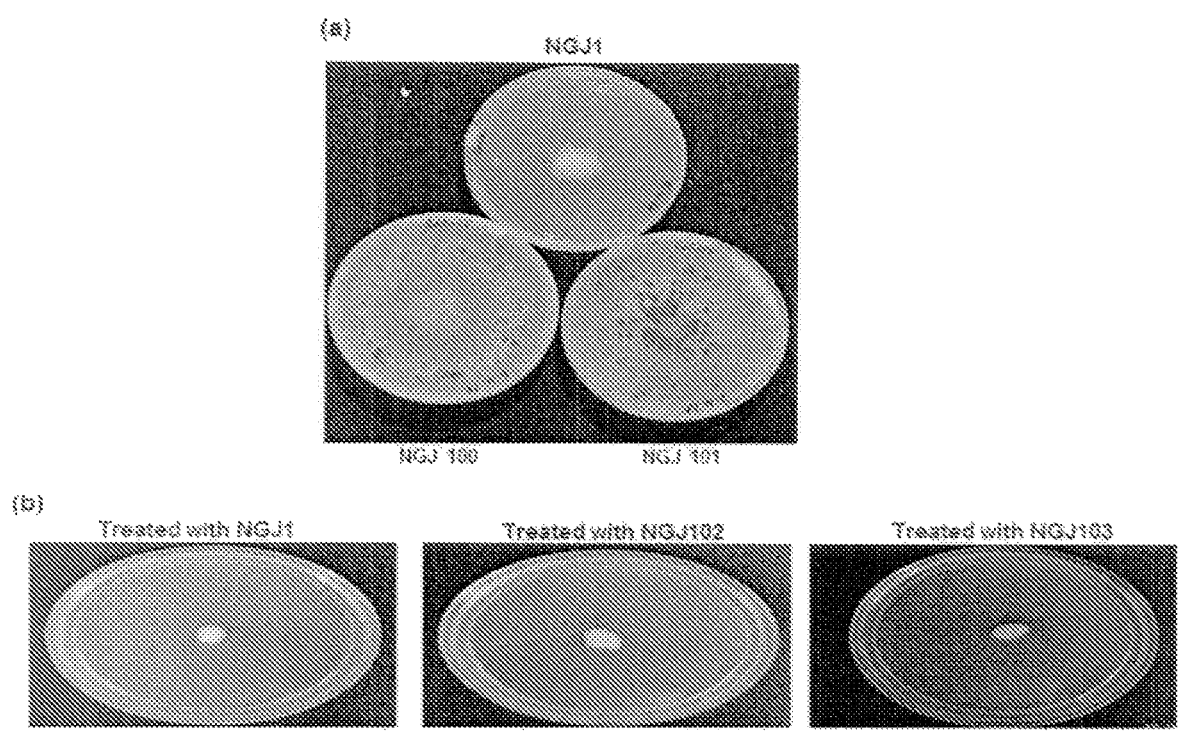

FIG. 6. Antifungal activity of Bg_9562 mutant and complementing *B. gladioli* strains. (a) Two independent mutants (NGJ100, NGJ101) of Bg_9562 were found defective in mycophagous activity, as they failed to prevent fungal growth. Notably treatment with wild type NGJ1 could prevent the growth of fungal sclerotia. (b) The complements NGJ102 and NGJ103 (expressing full length copy of the Bg_9562 gene on a broad host range plasmid, pHM1) were proficient to the level of wild type NGJ1 in demonstrating antibacterial/mycophagous activity of *R. solani*. The pictures depict the sclerotial growth after 7 days of different treatments.

DESCRIPTION OF THE INVENTION

While the invention is susceptible to various modifications and/or alternative processes and/or compositions, specific embodiment thereof has been shown by way of examples and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The examples, tables, and protocols have been represented where appropriate, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

In this specification and in the claims that follow, reference will be made to a number of terms that shall be defined to have the following meanings:

It must be noted that, as used in the specification/description and the appended claims and examples, the singular forms "a", "an" and "the" may include plural referents unless the context clearly dictates otherwise.

Ranges may be expressed herein as from "about" one particular value, and or "to about" another particular value. When such a range is expressed, another aspect includes from the one particular value and or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint.

The bacteria *Burkholderia gladioli* strain NGJ1 exhibiting fungal activity has been previously isolated from healthy rice seedling (Jha et al. 2015) and publically available expression vector pET28a that is commercially available from Novagen (Merck Life Science Private Limited) are used in the invention for expressing the novel sequence of Bg_9562. Therefore, the biological material is sufficiently described in the present invention.

The present invention provides novel genes and proteins capable of broad spectrum anti-fungal activities obtained from *Burkholderia gladioli* strain NGJ1 and its expression in pET28a expression vector.

As stated before, there remains a need for gene sequence of that exhibits broad-spectrum antifungal activity against several agriculturally important pathogens, including *Rhizoctonia solani, Magnaporthe oryzae, Venturia inaequalis*, and *Fusarium oxysporum*. Also, antifungal activity must be useful to treat animals as well as human disease caused by fungi.

Definitions

As used herein, the terms "Mycophagous behavior" when used in context of the present invention refers to the behavior of organisms that consume fungi.

As used herein, the terms "Antifungal behavior" when used in context of the present invention refers to treatment and prevention for mycoses such as athlete's foot, ringworm, candidiasis (thrush), serious systemic infections such as cryptococcal meningitis, and others against fungi.

As used herein, the terms "mutant" when used in context of the present invention refers to resulting from or showing the effect of mutation.

As used herein, the terms "insertion mutagenesis" when used in context of the present invention refers to mutagenesis of DNA by the insertion of one or more bases.

As used herein, the terms "reverse genetics approach" when used in context of the present invention refers to an approach to discover the function of a gene by analyzing the phenotypic effects of specific engineered gene sequences.

In one aspect, the present invention provides identification of novel protein having antifungal and mycophagous activity from *Burkholderia gladioli* strain NGJ1.

In another aspect, the present invention provides overexpression and purification of potential antifungal protein.

In yet another aspect, the present invention provides the process for assessment of antifungal activity of the novel protein. Still another aspect of the present invention provides establishment of the role of the antifungal protein through reverse genetics approach.

In one embodiment, the present invention relates to novel genes and proteins capable of broad spectrum anti-fungal activities. The novel genes expressing novel proteins from bacteria *Burkholderia gladioli* strain NGJ1 exhibit fungal eating (mycophagous) property. A nucleotide sequence encoding the novel protein is represented by sequence SEQ ID No. 1 and amino acid sequence of the novel protein is represented by the sequence SEQ ID No. 2.

In another embodiment, the present invention provides novel genetically engineered nucleotide sequence and peptide sequence of Bg_9562 gene that is capable of strong anti-fungal activity that further inhibit the growth of fungal sclerotia, induces cell death in fungal mycelia and treat humans/animals for fungal infections.

In an embodiment, the nucleotide sequence encoding the novel protein is at least 70% identical to the nucleotide sequence of SEQ ID No. 1 or the amino acid sequence represented by SEQ ID No. 2. In another embodiment, the nucleotide sequence of SEQ ID NO: 1 have at least 1 to 90 nucleotide acid substitutions, deletions, and/or insertions. In another embodiment, the amino acid sequence of SEQ ID NO: 2 have at least 1 to 30 amino acid substitutions, deletions, and/or insertions. In another embodiment, the amino acid sequence of SEQ ID NO: 2 have at least 2 to 20 amino acid substitutions, deletions, and/or insertions. In another embodiment, the amino acid sequence of SEQ ID NO: 2 have at least 2 to 15 amino acid substitutions, deletions, and/or insertions. In another embodiment, the amino acid sequence of SEQ ID NO: 2 have at least 5 to 15 amino acid substitutions, deletions, and/or insertions. In another embodiment, the amino acid sequence of SEQ ID NO: 2 varies by 11 amino acid substitutions. In another embodiment, in the amino acid sequence of SEQ ID no. 2 at least one or more Leucine, Valine, and/or Isoleucine residues are substituted.

In one embodiment, the novel protein imparts provides improved antifungal potency, broadened antifungal spectrum, improved solubility, improved thermos stability, and improved recombinant production compared to the wild type strain of *Burkholderia gladioli*. In one embodiment, the novel protein is adapted for broad spectrum anti-fungal activities and produces high mass production of proteins. In another embodiment, the amino acid sequence is of 111 residues long and has molecular weight of ~13 kDa, a pI of about 4.65 and a pH optimum at about 7.4.

In one embodiment of the invention, mutation of Bg_9562 gene through insertion mutagenesis results in loss of the antifungal activity and the mycophagous activity of the bacteria *Burkholderia gladioli* strain NGJ1. In another embodiment, the antifungal activity of Bg_9562 gene is useful for controlling sheath blight diseases of rice and other crops caused by *Rhizoctonia solani*.

In another embodiment of the invention insertion of full length copy of the gene could complement the defect and restored anti-fungal and mycophagous activity. One more aspect of the present invention provides the Bg_9562 gene encoding an antifungal protein that can be potentially used for controlling fungal disease. In another embodiment of the present invention, the anti-fungal activity of Bg_9562 is particularly against *Rhizoctonia solani* sclerotia that cause sheath blight disease in rice. In another embodiment of the present invention, the Bg_9562 induces cell death response in *Rhizoctonia solani* sclerotia.

In another aspect of the present invention the novel nucleotide sequence and peptide sequence are adapted to control diseases caused by *R. solani* on rice (sheath blight disease) as well as other crops (damping off of soyabean/tomato; black scurf of potato; root rot of sugarbeet; belly rot of cucumber; bair patch of cereals), fungal diseases of rice (sheath blight as well as rice blast), fungal diseases of plants (as mentioned in Table 1) and used to treat fungal infections of human/animals. For example, to treat candidiasis in humans/animals. In another aspect of the present invention, the novel nucleotide and protein are adapted to be used as spray or ointment for varied applications, as a transgene for developing broad spectrum fungal disease resistant rice as well as other important crops, engineering disease resistance in rice as well as other crops against *R. solani* infections. Additionally, the transgene can be used to provide disease resistance against other fungal pathogen infections.

TABLE 1

The list of fungi used for testing antifungal activity of Bg_9562 protein

| Sr. no. | Fungal strain | Disease |
| --- | --- | --- |
| 1 | *Rhizoctonia solani* | Sheath blight of rice/damping off of soyabean and tomato/black scurf of potato/root rot of sugarbeet/belly rot of cucumber/bair patch of cereals |
| 2 | *Alternaria brassicae* | Black spot of crucifers |
| 3 | *Magnaporthe oryzae* | Blast/blight disease of cereals |
| 4 | *Venturia inaequalis* | Apple scab disease |
| 5 | *Fusarium oxysporum* | Vascular wilt of tomato, tobacco, sweet potatoes, banana, legumes |
| 6 | *Dedymella* sp. | gummy stem blight of Cucurbits |
| 7 | *Phytophthora* sp. 7700 | potato blight, soya bean root/stem rot |
| 8 | *Colletotrichum* sp. | black spot disease of *Phaseolus* |
| 9 | *Ascochyta rabiei* | Blight disease of chickpea |
| 10 | *Neofusicoccum* sp. | stem-end rot of mango |
| 11 | *Alternaria* sp. | Brown Leaf Streak on Sugarcane |
| 12 | *Saccharomyces cerevisiae* | Model fungi |
| 13 | *Candida albicans* | Model fungi |

In another embodiment, the present invention further provides a method to prepare novel protein by SEQ ID No. 2 with antifungal activity. The method comprises the steps of: (i) protein possessing anti-fungal activity and mycophagous activity from *Burkholderia gladioli* strain is identified, (ii) gene and protein sequence from identified protein of step (i) is analysed by finding critical residues for antifungal as well as mass production and are artificially synthesized by gene synthesis, (iii) the evolved protein is over expressed in pET28a expression vector, (iii) the overexpressed protein is purified by Ni-NTA affinity chromatography, (iv) the purified protein is assessed for antifungal activity and (v) antifungal protein is established by reverse genetics approach. The recombinant expression of novel protein prevents the growth of fungal sclerotia and induces cell death in fungal mycelia.

In another embodiment of the present invention a composition comprising a novel peptide for use and development of water or oil based ointment or nano-encapsulated spray or antifungal film is provided. The components of the composition comprises oil that are selected from the group comprising of almond oil, rapeseed oil and sesame oil; thickeners that are selected from beeswax, cocoa butter and shea butter, emulsifiers selected from the group comprising of alcohols such as cetyl alcohol; and water.

In another embodiment, the composition is adapted to develop broad spectrum fungal disease resistance wherein the fungus is selected from the group comprising of *Rhizoctonia solani*, *Alternaria brassicae*, *Magnaporthe oryzae*, *Venturia inaequalis*, *Fusarium oxysporum*, *Dedymella* sp., *Phytophthora* sp, *Colletotrichum* sp., *Ascochyta rabiei*, *Neofusicoccum* sp., *Alternaria* sp., *Saccharomyces cerevisiae* and *Candida albicans*.

In another embodiment, a process to prepare the composition is provided. The process comprises the steps of: (i) Bg_9562 protein is produced in bulk quantities by fermentation using bioreactor, (ii) the fermented product obtained is encapsulated by chitosan or non-chitosan based nanoparticles; and (iii) the encapsulated products of step (ii) is used to develop a water base or an oil base cream/ointment and, (iv) the product of step (iii) are further developed to prepare antifungal films comprising starch/oils.

In another embodiment, the method to control fungal disease of plants or crops is provided by applying a polypeptide comprising the sequence of SEQ ID NO: 1 or 2, or a composition of any one of claims 12-13, to an infected plant, infected plant part, or infected crop that are at risk of fungal infection. The method also treat humans and animals. In another embodiment, the plant is a cereal, cucurbit, vegetable, root vegetable, or legume, or produces a fruit crop. In another embodiment, the plants or crops are selected from the group comprising of rice, soybean, tomato, potato, sugar beet, sugarcane, cucumber, apple, mango, *phaseolus*, tobacco, banana, legume, and chickpea.

In another embodiment the present invention provides a composition comprising the gene encoding novel peptide for use in developing transgenic plants (including rice) with broad spectrum disease resistance. The composition is used in developing rice resistance against sheath blight disease (caused by *R. solani*). Further, transgenic rice would also be resistant to blast disease (caused by *Magnaporthe oryzae* as protein also shows antifungal activity against *Magnaporthe oryzae* (as illustrated in Table 1). The composition also treats fungal infections in human/animals.

In another embodiment, a method to control antifungal disease is provided. The method comprises the steps of: (i) purified Bg_9562 protein is sprayed on the infected plants and nano-encapsulated form of the purified protein is sprayed onto the infected plants/fields; (ii) an antifungal cream is applied directly onto the disease lesion to control animal/human fungal infections and an antifungal film is applied as wound dressing to control fungal infections.

In another aspect of the present invention a non-naturally occurring novel protein or polypeptide of mutated sequence of Bg_9562 gene is provided. The novel proteins or polypeptide are adapted to exhibit antifungal activity by inhibiting growth of fungal sclerotia and inducing cell death in fungal mycelia. More specifically, the artificially developed novel nucleotide sequence of Bg_9562 gene and polypeptide or protein thereof is provided.

In another embodiment of the present invention a method to control sheath blight diseases of rice as well as other crops, method to control fungal diseases of rice, method to control fungal diseases of plants, method to treat fungal diseases of human/animal is provided.

In another aspect of the present invention method for development into spray or ointment for varied application, method for use as a transgene for developing disease resistance against fungal pathogens, method for controlling sheath blight disease of rice, as well as other important crops for developing broad spectrum fungal disease resistant plants.

In another embodiment, the protein is produced by expressing its encoding nucleotide in homologous or heterologous system in the cells of bacteria, yeasts, plants, humans and animals using recombinant DNA technology.

EXAMPLES

The following description is of exemplary embodiments only and is not intended to limit the scope, applicability or configuration to the invention in any way, Rather, the following description provides a convenient illustration for implementing exemplary embodiments of the invention various changes to the described embodiments may be made in the functions and arrangement of the elements described without departing from the scope of the invention.

Example 1: Identification of Protein Involved in Antifungal and Mycophagous Activity of *B. gladioli* Strain NGJ1

Figure 1:
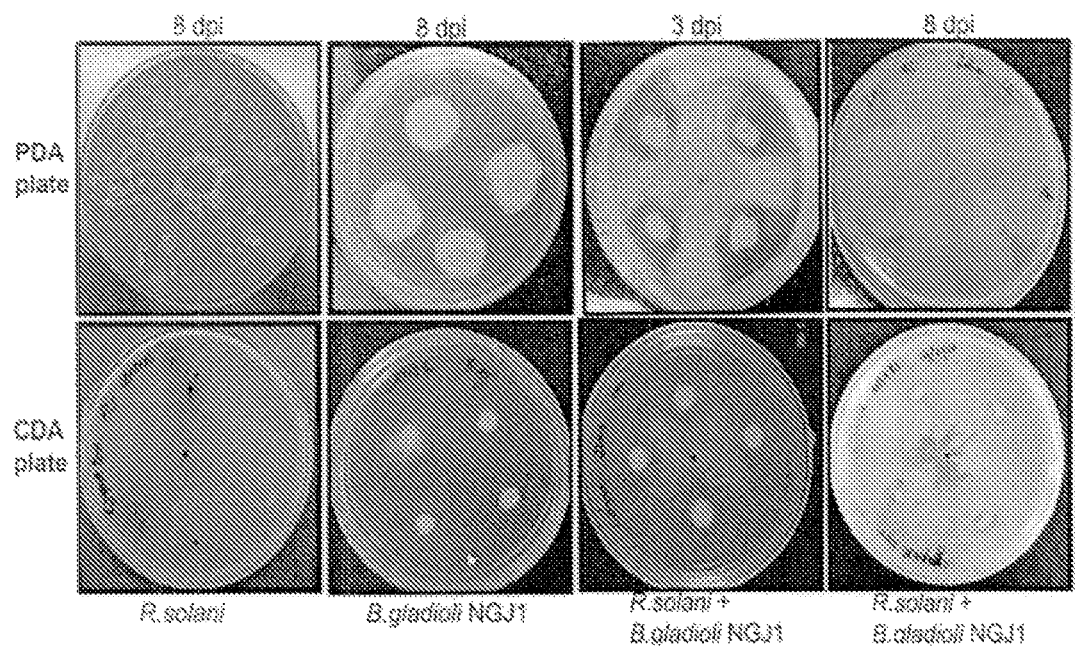
FIG. 1. Mycophagous and antifungal behavior of *Burkholderia gladioli* strain NGJ1 on *Rhizoctonia solani*. The *Burkholderia gladioli* strain NGJ1 inhibited fungal growth (formation of inhibition zone) during 3 dpi (days post inoculation) of co-cultivation. Subsequently at 8 dpi (days post inoculation), the bacterium is found growing over the entire fungal mycelia. Normal growth of the *R. solani* and NGJ1 (individually) was observed on PDA (Potato Dextrose Agar) plates. On CDA (Czapek Dox Agar) plates, *R. solani* grew (albeit slow) to cover the entire plate, but NGJ1 strain demonstrated very slow growth. However, upon confrontation with fungal mycelia, mycophagous behavior (bacterial spreading over fungi and degrading fungal mycelium) was very prolific on CDA plates.
Figure 2:
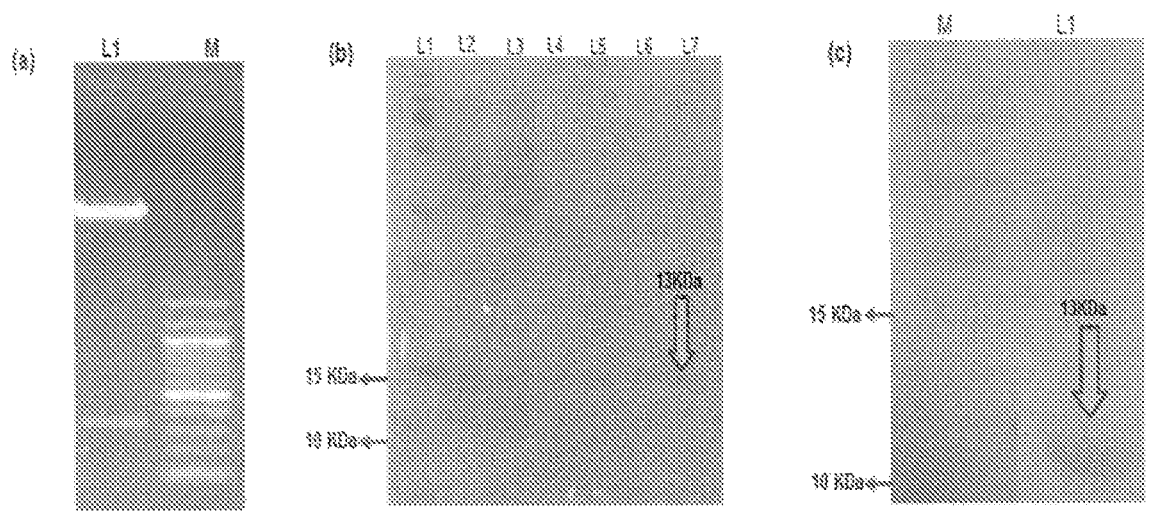
FIG. 2. Cloning and protein purification. (a) Restriction digestion conformation of Bg_9562 gene cloned in pET28a expression vector. (b) Purification of overexpressed protein by Ni2+-NTA-Agarose chromatography (L1—Marker, L2—flow through, L3—50 mM wash, L4 & L5—100 mM imidazole purification, L6 & L7—200 mM purification). (c) Western blotting of Bg_9562 protein with anti-His-antibody.
Figure 3:
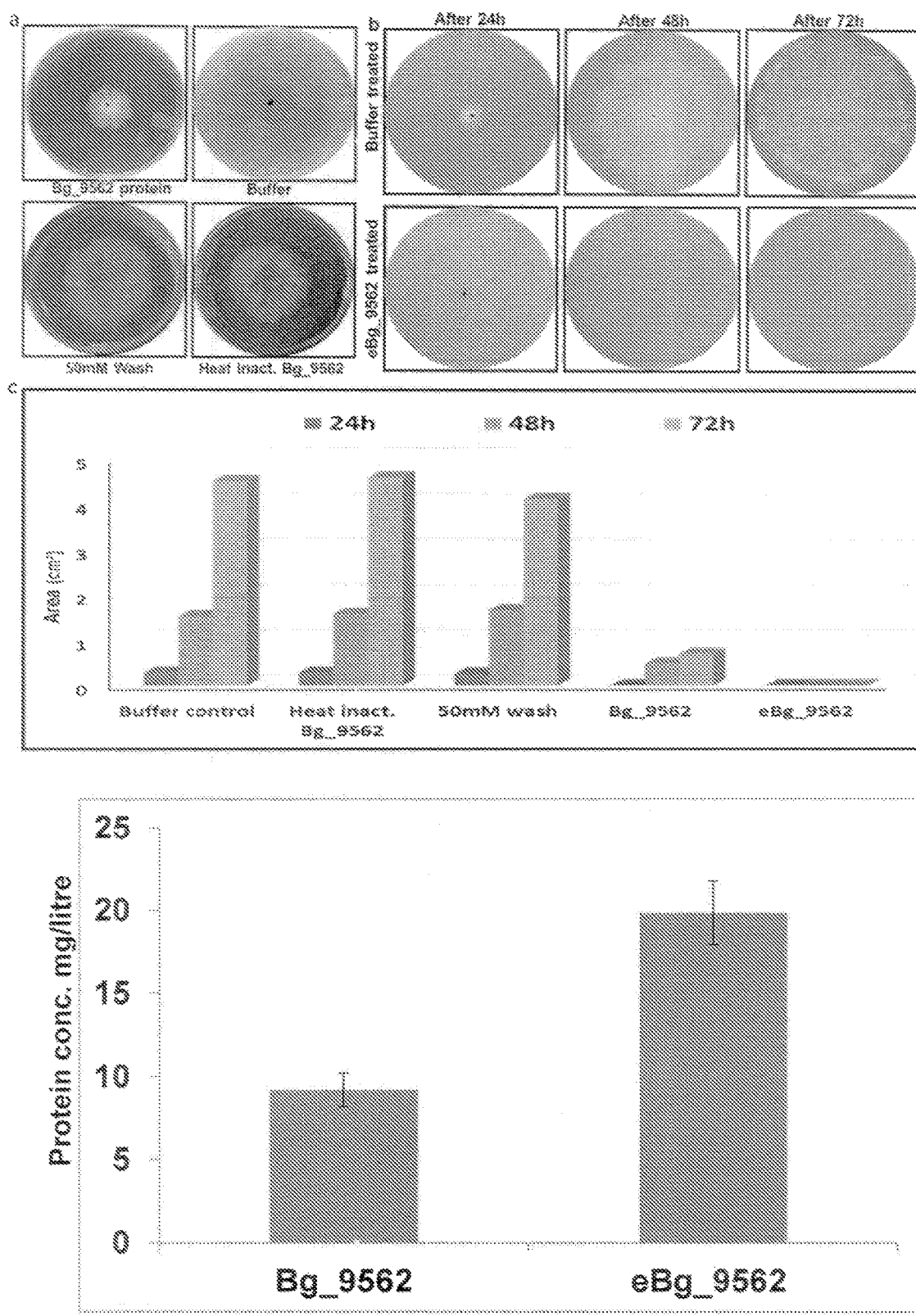
FIG. 3. Effect of Bg_9562 protein on sclerotial growth pattern. (a) *Rhizoctonia solani* sclerotia were treated with 15 µg/ml of Bg_9562 protein as well as different controls (Buffer control, 50 mM wash and Heat inactivated protein). The representative pictures of fungal growth on PDA plates at 48 h post treatment are depicted. (b) Fungal growth inhibition upon eBg_9562 protein treatment. 15 µg/ml of modified protein was efficient in preventing growth of *R. solani* on PDA plates while buffer treated sclerotia showed proper growth. The representative pictures of fungal growth at different time intervals are depicted. (c) Area of mycelial growth of *R. solani* at different time intervals after treatment of sclerotia with 15 µg/ml of Bg_9562 protein and eBg_9562 protein. The buffer, heat inactivated Bg_9562 and 50 mM wash were used as control (eBg_9562 protein is the evolved Bg_9562 protein). (d) protein estimation through Bradford suggesting enhanced production of eBg_9562 protein compared to wild Bg_9562.
Figure 4:
FIG. 4. MTT assay revealed Bg_9562 protein to induce cell death responses in fungi. (a) MTT assay of *R. solani* sclerotia after treatment with either 15 µg/ml of Bg_9562 protein or PBS buffer. The presence of brown pigment in the control suggested the live cells while the lack of color formation in protein treated samples suggested cell death in fungi.
Figure 5:
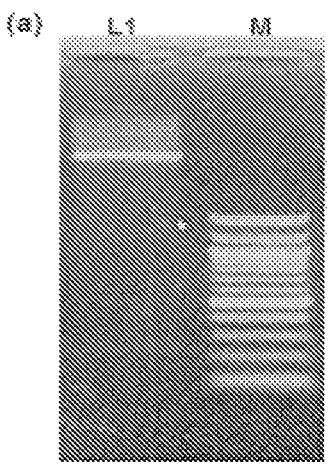
FIG. 5. Generating mutant *B. gladioli* defective in production of Bg_9562 protein. (a) The partial gene fragment of Bg_9562 gene was cloned in pK18 mob vector, picture depicts release of insert upon restriction digestion (b) the pK18 mob-9562 plasmid were mobilized into the NGJ1 genome and the recombinants were selected on antibiotic plates. The PCR amplicon obtained through colony PCR using gene specific.
Figure 5:
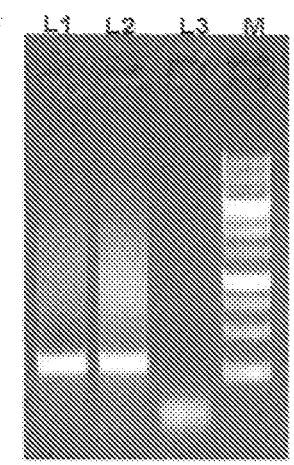

The present example provides identification of *Burkholderia gladioli* strain NGJ1 originated from healthy rice seedling (as described in Jha et al 2015) as a potent antifungal and mycophagous bacterium. Initially, up to 3 dpi (days post incubation) the bacterium show antifungal activity and prevent the growth of fungi in its vicinity. While during 8 dpi (days post incubation) of confrontation, the bacterium started foraging over fungi and demonstrated mycophagous activity (as shown in FIG. 1). Interestingly the mycophagous behavior (bacterial spreading over fungi and degrading fungal mycelium) was very prolific on minimal media CDA (Czapek Dox Agar) plates.

The inventors have found that some proteins of *Burkholderia gladioli* strain NGJ1 have potential signal for being targeted into host and one of such protein (Bg_9562) potentially encoding a phage tail protein was further characterized. The role of identification protein was studied with respect to mycophagous and antifungal behavior of *Burkholderia gladioli* strain NGJ1 on *Rhizoctonia solani*.

Some of the selected nucleotide sequences of Bg_9562 were modified to artificially synthesize evolved gene (eBg_9562) sequence having SEQ ID No. 1 made of 333 bp.

```
Bg_9562 (Nucleotide sequence): original
5'ATG AAC ACG GAA AAC CAG GAT CCG ACG AGC ACC AGC

GAC AAC GCC GCG AAC ACG CAC ACG CTC GAC ACG CCG

ATC GCG CGC GGC GAG CAG ACG ATC ACC CAG GTG ACG

CTG GCC AAG CCC GAT GCC GGC GCG CTG CGC GGC ACC

TCG CTG TCG GCG CTC GTC AAC CTC GAC GTC GAC GCG

CTG TGC AAG GTG CTG CCG CGC ATC ACG AGC CCG GCG

CTG ACC GCG GCC GAC GTG CGC GCC ATG GAC CCC GCC

GAC CTG GTC TCG CTG GGA GGC ATC TTC GCC GGT TTT

TTG ATG CCG AAG TCG CTG AAA GCG AGC ATG GAA

TCC CCG AGC GCG 3'

(Nucleotide sequence of evolved-Bg_9562)
                                       SEQ ID No. 1
5'ATG AAC ACG GAA AAC CAG GAT CCG ACG AGC ACC AGC

GAC AAC GCC GCG AAC ACG CAC ACG CTC GAC ACG CCG

CTC GCG CGC GGC GAG CAG ACG ATC ACC CAG GTG ACG

CTG GCC AAG CCC GAT GCC GGC GCG CTG CGC GGC ACC

TCG CTG TCG GCG CTC GTC AAC CTC GAC GTC GAC GCG

CTG TGC AAG GCA ACT CCG CGC GCT ACG AGC CCG GCG

GTC ACC GCG GCC GAC ATC CGC GCC ATG GAC CCC GCC

GAC GCA ATC TCG GTC GGA GGC ATC TTC GCC GGT TTT

GTT ATG CCG AAG TCG ATC AAA GCG AGC ATG GAA TCC

CCG AGC GCG 3'
```

Further novel peptide sequence of the above novel protein having SEQ ID No.2 made of 111 amino acids is provided.

Bg_9562 (Amino acid sequence): original

5' M N T E N Q D P T S T S D N A A N T H T L D T

P I A R G E Q T I T Q V T L A K P D A G A L R G T

S L S A L V N L D V D A L C K V L P R I T S P A L

T A A D V R A M D P A D L V S L G G I F A G F L M

P K S L K A S M E S P S A 3'

(Amino acid sequence of evolved-Bg 9562)

SEQ ID No. 2

5' M N T E N Q D P T S T S D N A A N T H T L D T

P L A R G E Q T I T Q V T L A K P D A G A L R G T

S L S A L V N L D V D A L C K A I P R A T S P A V

T A A D I R A M D P A D A I S V G G I F A G F V M

P K S I K A S M E S P S A 3'

The changes as highlighted from the parent protein are adapted for high mass production, improved solubility and antifungal activity of the evolved Bg_9562.

Example 2: Overexpression and Purification of Potential Antifungal Protein

The complete CDS of Bg_9562 gene (333 bp) was PCR amplified from *B. gladioli* strain NGJ1 genomic DNA using gene specific forward primer having SEQ ID No. 3 and reverse primer having SEQ ID No. 4 as disclosed in Table 2 and further cloned into pET28a bacterial expression vector (Novagen/Merck Life Science Private Limited) to obtain pET28a-9562 (as shown in FIG. 2*a*). The restriction sites of NdeI and HindIII had been added in the forward and reverse primer sequences, respectively.

Upon sequence validation, the pET28a-9562 was transformed into *E. coli* (BL21 strain, DE3-codon+) for recombinant protein production. The protein was purified using $Ni^{2+}$-NTA-Agarose chromatography and was resolved on SDS PAGE (as shown in FIG. 2*b*). Further it was electroblotted onto polyvinylidene fluoride (PVDF) membrane and probed with mouse polyclonal antibodies (1:1000 dilutions) raised against anti-His-antibody. The presence of ~13 KDa band suggested the overexpression and purification of the desired protein (as shown in FIG. 2*c*).

TABLE 2

Primer Sequences

| Primer Number* | Sequence | Restriction sites |
|---|---|---|
| Forward Primer: SEQ ID No. 3 | CATATGAACACGGAAAACCAG GAT | NdeI |
| Reverse Primer: SEQ ID No. 4 | AAGCTTCGCGCTCGGGGATTCC ATGCT | HindIII |
| Forward Primer- SEQ ID No. 5 | GAATTCATGCCGGCGCGCTGCG CGGC | EcoRI |
| Reverse Primer SEQ ID No. 6 | AAGCTTGCTCGGGGATTCCATG CTCGC | HindIII |
| Forward Primer SEQ ID No. 7 | AAGCTTAACACGGAAAACCAG GAT | HindIII |
| Reverse Primer SEQ ID No.8 | GAATTCCGCGCTCGGGGATTCC ATGCT | EcoRI |

*The primers were designed using PrimerQuest Tool of IDT (Integrated DNA technologies, Inc, U.S.A.; https://eu.idtdna.com/Primerquest/Home/Index) and synthesized from Eurofins Genomics India Pvt. Ltd., Bangalore, India). For cloning purpose, suitable restriction sites (marked as underlined) were incorporated at 5' end of selected primers to make them synthetic primers in nature.

Example 3: Assessing Antifungal Activity of the Purified Protein

Antifungal activity of protein having SEQ ID No.2 was assayed by treating *Rhizoctonia solani* strain BRS1 sclerotia with different concentrations (5, 10 and 15 μg/ml) of purified protein. As control, the sclerotia were treated with three different solutions 10 mM Phosphate buffer saline (PBS) pH 7.4, 50 mM wash (one component used in protein elusion) and heat inactivated Bg_9562 protein (by incubating in boiling water for 40 min). After treatment, sclerotia were placed on the PDA (Himedia, India) plates and incubated at 28° C. for further growth. Result (as shown in FIG. 3*a*) summarizes that 15 μg/ml of the protein was efficient in preventing the growth of *R. solani*, while proper fungal growth was observed in case of different controls. Fungal growth inhibition upon eBg_9562 protein treatment is summarized in FIG. 3*b*. The eBg_9562 treated sclerotia failed to grow while the control sclerotia showed proper growth. Further, upon different time intervals (such as 24 h, 48 h and 72 h), sclerotial growth in terms of area of the mycelial lawn on PDA plates for both Bg_9562 as well as eBg_9562 protein treated along with various control treated samples were measured and data is summarized in FIG. 3*c*. Overall, the data clearly demonstrate that in comparison to Bg_9562, the eBg_9562 is more efficient in preventing the fungal growth. Further, Table 3 represents the tabulated data showing the comparison fungal growth inhibition upon various treatments (as referred in FIG. 3*c*).

TABLE 3

Fungal growth inhibition upon various treatments

| | Observed growth area ($cm^2$) | | |
|---|---|---|---|
| Sample | 24 h | 48 h | 72 h |
| Buffer control | 0.28 | 1.53 | 4.52 |
| Heat inactivated. Bg_9562 | 0.28 | 1.57 | 4.60 |
| 50 mM wash buffer | 0.25 | 1.66 | 4.13 |
| Bg_9562 | 0.00 | 0.48 | 0.69 |
| eBg_9562 | 0.00 | 0.00 | 0.00 |

Table 3 depicts that after 72 hours of growth upon treatment with evolved Bg_9562, the fungi shows nil growth against fungi treated with wild type Bg_9562 protein that shows the growth of 0.69 $cm^2$ after 72 hours of treatment. Notably various control treatments do not inhibit the growth of fungi. Therefore, the present invention provides novel genes and proteins that are capable of broad spectrum anti-fungal activities. The novel genes and proteins are obtained from Burkholderia gladioli strain NGJ1 and expressed in pET28a expression vector. The eBg_9562 is effective and provides nil anti-fungal activity even after 72 hours of its treatment under various conditions (as depicted by FIG. 3*c*). The modification in the protein has led to enhanced protein production as confirmed by protein estimation data through Bradford in FIG. 3*d*. The figure depicts that the protein concentration of eBg_9562 is nearly 20 mg/liter compared to the protein concentration of wild Bg_9562 that produces less than 10 mg/liter of protein.

Furthermore, *R. solani* sclerotia were initially grown in PDB media for 48 h to have germinating mycelia and then subjected to treatment with 15 μg/ml of Bg_9652 protein and 10 mM PBS buffer (as a control). Upon further incubation at 28° C., the treated and control mycelia were subjected to MTT assay as per the protocol described (Meshulam et al, 1995). Result of MTT assay suggested that the protein treatment could induce cell death as there was no formation of colored compound (as shown in FIG. 4*a*). While due to active metabolism, formation of colored compound was detected in case of control mycelia (as shown in FIG. 4*a*).

Example 4: Establishing the Role of the Antifungal Protein Through Reverse Genetics Approach In order to demonstrate that the SEQ ID No. 2 protein is indeed involved in antifungal and mycophagous behaviors of *B. gladioli* strain NGJ1, we adopted reverse genetics approach. For this the pGD1 plasmid was obtained by cloning 209 bp of the wild type Bg_9562 gene using a Forward primer having SEQ ID No. 5 and reverse primer having SEQ ID No. 6 as disclosed in Table 1 into pK18 mob vector (Schäfer A et al, 1994). The pGD1 was mobilized into *B. gladioli* strain NGJ1 by using published protocol (Schäfer A et al, 1990) and the selection of 49562 insertion mutants (NGJ100 and NGJ101) were performed on kanamycin (50 μg/μ1) containing PDA plates. The 49562 insertion mutant bacterium was confirmed through PCR and sequencing (as shown in FIG. 5*a* &5b).

Further for complementation, full lengths of the gene was amplified from NGJ1 genome by using forward primer having SEQ ID No. 7 and reverse primer having SEQ ID No. 8 as disclosed in Table 2 and cloned into pHM1 vector. The pHM1-9562 plasmid was electroporated into NGJ100 and NGJ101 strain and positive $Kan^R$ and $Spec^R$ colonies were selected on KBA plates. The NGJ100 and NGJ101 containing pHM1-9562 complementing plasmid (NGJ102 and NGJ103) was further confirmed through PCR and sequencing.

After, both Bg_9562 mutants (NGJ100 and NGJ101) and complementing (NGJ102 and NGJ103), *B. gladioli* strains were tested for the anti-fungal and mycophagous activity of *R. solani*. The mutant bacterium failed to demonstrate the antifungal and mycophagous activity {as shown in (FIG. 6*a*)}. Fungal sclerotia were treated with the bacterial cultures of Bg_9562 mutants (NGJ100 and NGJ101), complements (NGJ102 and NGJ103) and wild type NGJ1 (WT) individually for 4 hours at 28° C. followed by subsequent incubation on PDA plates for 7 days (as shown in (FIG. 6*b*)).

Example 5: The Protein Demonstrate Broad Spectrum Antifungal Activities

The effect of purified proteins was also tested on various fungi including several agricultural important fungal pathogens (as illustrated in Table 1) and the experimental data as evident by FIG. 3 and Table 3 of the specification.

REFERENCES

Afsharmanesh H, Ahmadzadeh M, Sharifi-Tehrani A (2006) Biocontrol of *Rhizoctonia solani*, the causal agent of bean damping-off by fluorescent pseudomonads. Commun Agric Appl Biol Sci. 71:1021-1029

Andersen J B, Koch B, Nielsen T H, Sorensen D, Hansen M, Nybroe O, Christophersen C, Sorensen J, Molin S, Givskov M (2003) Surface motility in *Pseudomonas* sp. DSS73 is required for efficient biological containment of the root-pathogenic microfungi *Rhizoctonia solani* and *Pythium ultimum*. *Microbiology* 149: 37-46

Beneduzi A, Ambrosini A, Passaglia L M P (2012) Plant growth-promoting rhizobacteria (PGPR): Their potential as antagonists and biocontrol agents. Genetics and Molecular Biology 35: 1044-1051.

Compant S, Duffy B, Nowak J, Clement C, Barka E A (2005) Use of plant growth-promoting bacteris for biocontrol of plant disease: Principles, mechanism of action, and future prospects. Appl Environ Microbiol. 71:4951-4959.

Elshafie H S, Camele I, Racioppi R, Scrano L, lacobellis N S, *Bufo* S A (2012) In vitro antifungal activity of *Burkholderia gladioli* pv. agaricicola against some Phytopathogenic fungi. Int J Mol Sci. 13: 16291-16302

Frey-Klett P, Burlinson P, Deveau A, Barret M, Tarkka M, Sarniguet A (2011) Bacterial-Fungal Interactions: Hyphens between Agricultural, Clinical, Environmental, and Food Microbiologists. MMBR. 75(4):583-609. doi: 10.1128/MMBR.00020-11

Ghosh S, Gupta S K, Jha G (2014) Identification and functional analysis of AG1-IA specific genes of *Rhizoctonia solani*. Curr Genet. 60: 327-341

Haas D, Défago G (2005) Biological control of soil-borne pathogens by fluorescent pseudomonads. Nat Rev Microbiol. 3: 307-319

Hane J K, Anderson J P, Williams A H, Sperschneider J, Singh K B (2014) Genome Sequencing and Comparative Genomics of the Broad Host-Range Pathogen *Rhizoctonia solani* AG8. PLoS Genet. doi: 10.1371/journal.pgen.1004281

Haung D, Ou B, Prior R L (2005) The chemistry behind antioxidant capacity assays. J. Agric. Chem. 53: 1841-1856.

Höppener-Ogawa S, Leveau J H J, van Veen J a, De Boer W (2009) Mycophagous growth of Collimonas bacteria in natural soils, impact on fungal biomass turnover and interactions with mycophagous *Trichoderma* fungi. ISME J. 3: 190-198

Huang X, Zhang N, Yong X, Yang X, Shen Q (2012) Biocontrol of *Rhizoctonia solani* damping-off disease in cucumber with *Bacillus pumilus* SQR-N43. Microbiol Res. 167: 135-143

Jha G, Tyagi I, Kumar R, Ghosh S (2015) Draft Genome Sequence of Broad-Spectrum Antifungal Bacterium *Burkholderia gladioli* Strain NGJ1, Isolated from Healthy Rice Seeds. Genome Announc. doi: 10.1128/genomeA.00803-15

Kishore G K, Pande S, Podile A R (2005) Biological control of collar rot disease with broad-spectrum antifungal bacteria associated with groundnut. Can J Microbiol. 51:123-132

Leveau J H J, Preston G M (2008) Bacterial mycophagy: definition and diagnosis of a unique bacterial-fungal interaction. New Phytol. 177: 859-876

Li J, Yang Q, Zhao L, Zhang S, Wang Y, Zhao X (2009) Purification and characterization of a novel antifungal protein from *Bacillus subtilis* strain B29. Journal of Zhejiang University Science B. 10(4):264-272.doi: 10.1631/jzus. B0820341

Lugtenberg B, Kamilova F (2009) Plant-growth-promoting rhizobacteria. Annu. Rev. Microbiol. 63:541-556

Manwar A V, Khandelwal S R, Chaudhari B L, Meyer J M, Chincholkar S B (2004) Siderophore production by a marine *Pseudomonas aeruginosa* and its antagonistic action against phytopathogenic fungi. Appl Biochem Biotechnol. 118: 243-251

Mela F, Fritsche K, de Boer W, van Veen J a, de Graaff L H, van den Berg M, Leveau J H J (2011) Dual transcriptional profiling of a bacterial/fungal confrontation: Collimonas fungivorans versus *Aspergillus niger*. ISME J. 5: 1494-1504

Meshulam T, Levitz S M, Christin L, Diamond R D (1995) A simplified new assay for assessment of fungal cell damage with the tetrazolium dye, (2,3)-bis-(2-methoxy-4-nitro-5-sulphenyl)-(2H)-tetrazolium-5-carboxanil ide (XTT). J Infect Dis. 4:1153-1160.

Nagarajkumar M, Bhaskaran R, Velazhahan R (2004) Involvement of secondary metabolites and extracellular lytic enzymes produced by *Pseudomonas fluorescens* in inhibition of *Rhizoctonia solani*, the rice sheath blight pathogen. Microbiol Res. 159:73-81

Raaijmakers J M, Mazzola M (2012) Diversity and Natural Functions of Antibiotics Produced by Beneficial and Plant Pathogenic Bacteria. Annu Rev Phytopathol. 50: 403-424

Reinhold-Hurek B, Hurek T (2011) Living inside plants: bacterial endophytes. Curr Opin Plant Biol. 14:435-443

Schäfer A, Kalinowski J, Simon R, Seep-Feldhaus A H, Paler A (1990) High-frequency conjugal plasmid transfer from gram-negative *Escherichia coli* to various gram-positive coryneform bacteria. J Bacteriol. 172(3):1663-1666

Schäfer A, Tauch A, Jager W, Kalinowski J, Thierbach G, Paler A (1994) Small mobilizable multi-purpose cloning vectors derived from the *Escherichia coli* plasmids pK18 and pK19: selection of defined deletions in the chromosome of *Corynebacterium glutamicum*. Gene 145(1):69-73

Sharifi-Tehrani A, Shakiba M, Okhovat M, Zakeri Z (2005) Biological control of Tiarosporella *phaseolina* the causal agent of charcoal rot of soybean. Commun Agric Appl Biol Sci. 70:189-192

Tan Z, Lin B, Zhang R (2013) A novel antifungal protein of *Bacillus subtilis* B25. Springer Plus 2:543. doi: 10.1186/2193-1801-2-543

Tang-Bing Cui, Hai-Yun Chai, Li-Xiang Jiang. (2012) Isolation and Partial Characterization of an Antifungal Protein Produced by *Bacillus licheniformis* BS-3. Molecules. 17(6):7336-7347

Tortora M L, Diaz-Ricci J C, Pedraza R O (2011) Azospirillum brasilense siderophores with antifungal activity against *Colletotrichum acutatum*. Archives of Microbiology 193: 275-286

Wong J H1, Hao J, Cao Z, Qiao M, Xu H, Bai Y, Ng T B (2008) An antifungal protein from *Bacillus amyloliquefaciens*. J Appl Microbiol. 105(6):1888-1898

Yadav V, Mandhan R, Kumar M, Gupta J, Sharma G L (2010) Characterization of the *Escherichia coli* Antifungal Protein PPEBL21. Int J Microbiol. 196363. doi: 10.1155/2010/196363

Zheng A, Lin R, Zhang D, Qin P, Xu L, Ai P, Ding L, Wang Y, Chen Y, Liu Y, et al. (2013) The evolution and pathogenic mechanisms of the rice sheath blight pathogen. Nat Commun. 4:1424. doi: 10.1038/ncomms2427.

The invention claimed is:

1. A novel protein comprising an amino acid sequence of SEQ ID No. 2 wherein said amino acid is encoded by the nucleotide sequence of SEQ ID No. 1.

2. The protein of claim 1, wherein the amino acid sequence and the nucleotide sequence are non-naturally occurring and genetically engineered from wild *Burkholderia gladioli* Bg_9562 gene.

3. The protein of claim 1, for use in treatment of fungal diseases.

4. The protein of claim 1, having amino acid sequence of SEQ ID No. 2 of 111 amino acid residues long with a molecular weight of at least ~13 kDa, a pI of about 4.65 and a pH optimum at about 7.4.

5. The protein of claim 1, for use in inhibiting growth of fungi and inducing cell death in fungal mycelia.

6. The protein of claim 1, for use in controlling fungal diseases in crops, preferably sheath blight disease of rice caused by *Rhizoctonia solani.*

7. The protein of claim 1, wherein the protein is produced by expressing its encoding nucleotide in the cells of bacteria, yeast, insects, plants, humans or animals using recombinant DNA technology.

8. A method to prepare novel protein for anti-fungal activity represented by sequence SEQ ID No. 2, wherein the method comprising the steps of:

(i) identifying the protein that possess antifungal activity and mycophagous activity from wild *Burkholderia gladioli* strain NGJ1, (ii) analyzing amino acid sequence of the encoded protein by finding critical residues associated with anti-fungal activity as well as mass production, and artificially designing gene sequence to incorporate desired change in the identified protein of step (i) and synthesizing the designed gene through gene synthesis, (iii) over expressing evolved protein of step (ii) in an expression vector to get recombinant protein, (iv) purifying the over expressed protein of step (iii) by chromatography, (v) assessing the antifungal activity of purified protein of step (iv), and (vi) establishing antifungal activity of protein role by reverse genetics approach to obtain the novel protein from Bg_5672.

9. A composition comprising the protein of claim 1 for antifungal activity wherein the composition further comprises an oil selected from the group comprising of almond oil, rapeseed oil and sesame oil; thickeners selected from beeswax, cocoa butter and shea butter; emulsifiers selected from the group comprising of alcohols such as cetyl alcohol; and water.

10. The composition as claimed in claim 9 used for controlling fungal disease wherein the fungus is selected from the group comprising *Rhizoctonia solani, Magnaporthe oryzae, Saccharomyces cerevisiae* and *Candida albicans.*

11. A process for preparing composition for antifungal activity, wherein the process comprising steps:

(i) producing evolved Bg_9562 protein represented by sequence SEQ ID No. 2 in bulk quantities by fermentation in bioreactor;

(ii) encapsulating the fermented product of step (i) in chitosan or non-chitosan based nanoparticles;

(iii) using the encapsulated product of step (ii) to develop water base or oil base cream/ointment; and (iv) converting the product of step (iii) to antifungal peptide comprising films made from starch/oils.

12. A method for controlling fungal disease of plants or crops, comprising: applying a polypeptide comprising the sequence of SEQ ID NO: 2, or a composition of claim 9, to an infected plant, infected plant part, or infected crop.

* * * * *